(12) United States Patent
Zavislan

(10) Patent No.: US 7,225,010 B1
(45) Date of Patent: *May 29, 2007

(54) SYSTEM AND METHOD FOR CONFOCAL IMAGING WITHIN DERMAL TISSUE

(75) Inventor: James M. Zavislan, Pittsford, NY (US)

(73) Assignee: Lucid, Inc., Rochester, NY (US)

( * ) Notice: Subject to any disclaimer, the term of this patent is extended or adjusted under 35 U.S.C. 154(b) by 75 days.

This patent is subject to a terminal disclaimer.

(21) Appl. No.: 09/658,736

(22) Filed: Sep. 11, 2000

Related U.S. Application Data

(62) Division of application No. 08/942,431, filed on Oct. 1, 1997, now Pat. No. 6,424,852.

(60) Provisional application No. 60/028,847, filed on Oct. 18, 1996.

(51) Int. Cl.
A61B 5/00 (2006.01)

(52) U.S. Cl. .................. 600/407; 600/425; 600/476

(58) Field of Classification Search .......... 600/407, 600/425, 473, 476, 587, 415, 417, 421, 429
See application file for complete search history.

(56) References Cited

U.S. PATENT DOCUMENTS

| | | |
|---|---|---|
| 4,385,634 A | 5/1983 | Bowen |
| 4,442,844 A | 4/1984 | Navach |
| 4,515,165 A | 5/1985 | Carroll |
| 4,570,638 A | 2/1986 | Stoddart et al. |
| 5,120,953 A | 6/1992 | Harris |
| 5,146,923 A | 9/1992 | Dhawan |
| 5,195,522 A | 3/1993 | Pytel et al. |
| 5,349,961 A | 9/1994 | Stoddart et al. |
| 5,371,368 A | 12/1994 | Alfano et al. |
| 5,524,636 A | 6/1996 | Sarvazyan et al. |
| 5,557,452 A | 9/1996 | Harris |

(Continued)

FOREIGN PATENT DOCUMENTS

AU A-11045/88 8/1988

(Continued)

OTHER PUBLICATIONS

Jester et al, In-Vivo Real-Time Confocal Imaging, Journal Of Electron Microscopy Technique, vol. 18, No. 1, pp. 50-60, May 1991.*

(Continued)

Primary Examiner—Ruth S. Smith
(74) Attorney, Agent, or Firm—Kenneth J. Lukacher; Martin Lukacher

(57) ABSTRACT

An improved system for confocal imaging within dermal tissue of a patient is provided which minimizes instability in confocal images by reducing the relative motion of the tissue with respect to the confocal imaging optics of the system. The system includes a mechanism for maintaining an area of skin tissue under stress by application of force at the edges of the area, and an imaging head coupled to this mechanism for imaging the stressed skin. The mechanism includes a mechanical structure, such as a platen, brace, or attachment, which both supports the imaging head of the system and applies stress to a limited surface area of the tissue to minimize skin motion during confocal imaging.

35 Claims, 10 Drawing Sheets

U.S. PATENT DOCUMENTS

| | | |
|---|---|---|
| 5,606,971 A | 3/1997 | Sarvazyan |
| 5,701,902 A | 12/1997 | Vari et al. |
| 5,719,700 A | 2/1998 | Corcuff et al. |
| 5,722,398 A | 3/1998 | Ishihara et al. |
| 5,730,133 A | 3/1998 | Godik |
| 5,769,076 A | 6/1998 | Maekawa et al. |
| 5,787,887 A | 8/1998 | Klingenbeck-Regn |
| 5,788,634 A | 8/1998 | Suda et al. |
| 5,788,639 A | 8/1998 | Zavislan et al. ............ 600/476 |
| 5,833,633 A | 11/1998 | Sarvazyan |
| 5,833,634 A | 11/1998 | Laird et al. |
| 5,840,023 A | 11/1998 | Oraevsky et al. |
| 5,842,995 A | 12/1998 | Mahadevan-Jansen et al. |
| 5,848,177 A | 12/1998 | Bauer et al. |
| 5,851,181 A | 12/1998 | Talmor |
| 5,860,967 A | 1/1999 | Zavislan et al. |
| 5,880,880 A | 3/1999 | Anderson et al. |
| 5,995,283 A | 11/1999 | Anderson et al. |
| 5,999,836 A | 12/1999 | Nelson et al. |
| 6,032,071 A | 2/2000 | Binder |
| 6,197,575 B1 | 3/2001 | Griffith et al. |
| 6,263,233 B1 | 7/2001 | Zavislan et al. |
| 6,937,886 B2 * | 8/2005 | Zavislan .................... 600/476 |

FOREIGN PATENT DOCUMENTS

| | | |
|---|---|---|
| CH | 669 325 A5 | 3/1989 |
| DE | 32 31 483 A1 | 3/1984 |
| EP | 0 683 386 A1 | 11/1995 |
| WO | WO 88/05284 | 7/1988 |
| WO | WO 96/21938 | 7/1996 |

OTHER PUBLICATIONS

Rajadhyaksha, et al., "In Vivo Confocal Scanning Laser Microscopy of Human Skin: Melanin Provides Strong Contrast" The Journal of Investigative Dermatology, vol. 104, No. 6, Jun. 1995, pp. 1-7.

Brochure on EpiScope Skin Surface Microscope Manufactured by Welch Allyn, Skaneateles Falls, NY.

Brochure on DermaScope Manufactured by Bio-Rad Micromeasurements, Inc., Cambridge, Mass.

Brumberg et al., "Hand-held contact microscope for medical applications," Soviet Journal of Optical Technology, Jan. 1974, vol. 41, No. 1.

Corcuff et al., Morphometry of human epidermis in vivo by real-time confocal microscopy, Arch Dermatol Res. 1993, 285, pp. 475-481.

Corcuff et al., In vivo Vision of the Human Skin with the Tandem Scanning Microscope, Dermatology, vol. 186, pp. 50-54, (1993).

Delaney et al., Fibre Optic Confocal Imaging (FOCI) for subsurface microscopy of the colon in vivo, J. Anat. 184, pp. 157-160, (1994).

Delaney et al., Novel Microscopy Using Fibre Optic Confocal Imaging and Its Suitability for Subsurface Blood Vessel Imaging in Vivo, Clinical and Experimental Pharmacology and Physiology, 20, pp. 197-198, (1993).

Koester, C., Scanning mirror microscope with optical sectioning characteristics: applications in ophthalmology, Applied Optics, vol. 19, No. 11, pp. 1749-1757, 1980.

Maurice, D., Cellular Membrane Activity in the Corneal Endothelium of the Intact Eye, Experientia, vol. 24, No. 11, pp. 1094-1095, 1968.

New, K. et al., In Vivo Imaging of Human Teeth and Skin Using Real-Time Confocal Microscopy, Scanning; vol. 13, pp. 369-372, 1991.

* cited by examiner

SYSTEM AND METHOD FOR CONFOCAL IMAGING WITHIN DERMAL TISSUE

This application is a divisional of U.S. patent application Ser. No. 08/942,431, filed Oct. 1, 1997, now U.S. Pat. No. 6,424,852, which claims the benefit of priority to U.S. Provisional Application Ser. No. 60/028,847, filed Oct. 18, 1996.

FIELD OF THE INVENTION

The present invention relates to a confocal imaging system for in vivo clinical examinations of dermal and subdermal tissues, and particularly to a confocal imaging system of a patient's skin tissue which minimizes instability in confocal images by reducing the relative motion of the tissue with respect to the confocal imaging optics of the system. This invention is especially suitable for providing an instrument or attachment for dermal pathological applications.

BACKGROUND OF THE INVENTION

Systems have been proposed for confocal scanning of skin, such as described in Rajadhyaksha et al., "In vivo Confocal Scanning Laser Microscopy of Human Skin: Melanin provides strong contrast." The Journal of Investigative Dermatology, Volume 104, No. 6, June 1995, pages 1–7. These systems have confocal optics which direct light to the patient's skin tissue and image the returned reflected light. Such optics have a limited field of view of the patient's skin tissue, which for example may cover a tissue area less than one millimeter wide. One problem with these systems is that motion of the patient during confocal imaging can cause the tissue area being imaged to move relative to the system's confocal optics, shifting the field of view of the tissue area with respect to the optics. Consequently, confocal images from such systems may appear unstable to the viewing physician, making it difficult for the physician to observe dermal structures of interest. Even slight motion of the patient's skin tissue, such as due to involuntary muscle movement in adjacent tissue or from a circulatory pulse, can cause dermal structures of a confocal image to appear to move in and out of the imaged tissue area.

SUMMARY OF THE INVENTION

Accordingly, it is the principal object of the present invention to provide an improved system for confocal imaging within dermal and subdermal tissue of a patient which minimizes instability in confocal images by reducing the relative motion of the tissue with respect to the confocal imaging optics of the system.

It is another object of the present invention to provide an improved system for confocal imaging of tissue having a mechanical structure, such as a platen, brace, or attachment which both supports the confocal imaging optics of the system and applies stress to a limited surface area of the tissue to minimize skin motion during confocal imaging.

Briefly described, the system embodying the present invention includes a mechanism for maintaining an area of skin tissue under stress by application of force at the edges of the area, and an imaging head coupled to this mechanism for imaging the stressed skin. The mechanism and imaging head provide an integrated assembly. In one embodiment, the mechanism of the system for maintaining an area of skin tissue under stress is provided by a platen. which is positionable with respect to the patient having the skin tissue to be examined. The imaging head is coupled to the platen and is positioned for imaging through an orifice in the platen. To position the platen with respect to the patient, the patient is supported by a table and the platen rides in a carriage upon rails over the patient. The carriage and platen assembly may be temporarily locked in position upon the rails. Another mechanism is provided in the system for moving the platen from an up position in the carriage, where the platen is spaced from the patient, to a down position onto the surface of the skin tissue of the patient, such that in the down position the force of the platen stresses the skin tissue within the orifice of the platen.

In a second embodiment, the mechanism of the system for maintaining an area of skin tissue under stress is provided by a brace supporting the imaging head. The brace has an opening through which the imaging head images the skin tissue. The brace is restrained by straps to the body part of the patient having the skin tissue in order to force the brace against the skin tissue, thereby stressing the skin tissue within the opening of the brace. The brace may further include an upper lamination, coupled to the imaging head, and a lower lamination, coupled to the restraining straps, which provides the opening of the brace. The lower lamination has slots for receiving the upper lamination in which the upper lamination is movable within the slots over the lower lamination and temporarily fixable within respect to the lower lamination. The upper lamination has an aperture (or window) substantially smaller than the opening in the lower lamination. Through the aperture of the upper lamination, the imaging head images the stressed skin tissue within the opening of the lower lamination.

In a third embodiment, the mechanism of the system for maintaining an area of skin tissue under stress is provided by an attachment having an inner window member and a flexible diaphragm member extending radially from the inner member. A suction mechanism is provided for creating a vacuum between the attachment and the surface of the skin tissue to force the skin tissue against the inner member, thereby stressing the skin tissue adjacent to the inner member. The imaging head images the stressed skin tissue through the window member. The diaphragm member may further include a semi-rigid ring along its outer periphery and an annular protruding section which defines inner and outer cavities when the attachment is adjacent to the skin tissue. The suction mechanism may then selectively create suction in the inner and outer cavities, when the attachment is adjacent to the skin tissue, to pull the skin tissue into the cavities and stress the skin tissue adjacent to the inner member.

The three embodiments of the system are particularly suitable for imaging external tissue in different regions of the patient's body. The platen may be used for confocal imaging of skin tissue on the chest or back. The brace may be used for gross anatomical features, such as the arm, leg or torso, around which the straps can hold the brace upon. The attachment is useful for smaller regions of the skin, where there is no gross anatomical feature, or where the surface of the skin tissue in not substantially level.

BRIEF DESCRIPTION OF THE DRAWINGS

The foregoing objects, features and advantages of the invention will become more apparent from a reading of the following description in connection with the accompanying drawings in which.

DETAILED DESCRIPTION OF THE INVENTION

Figure 1:
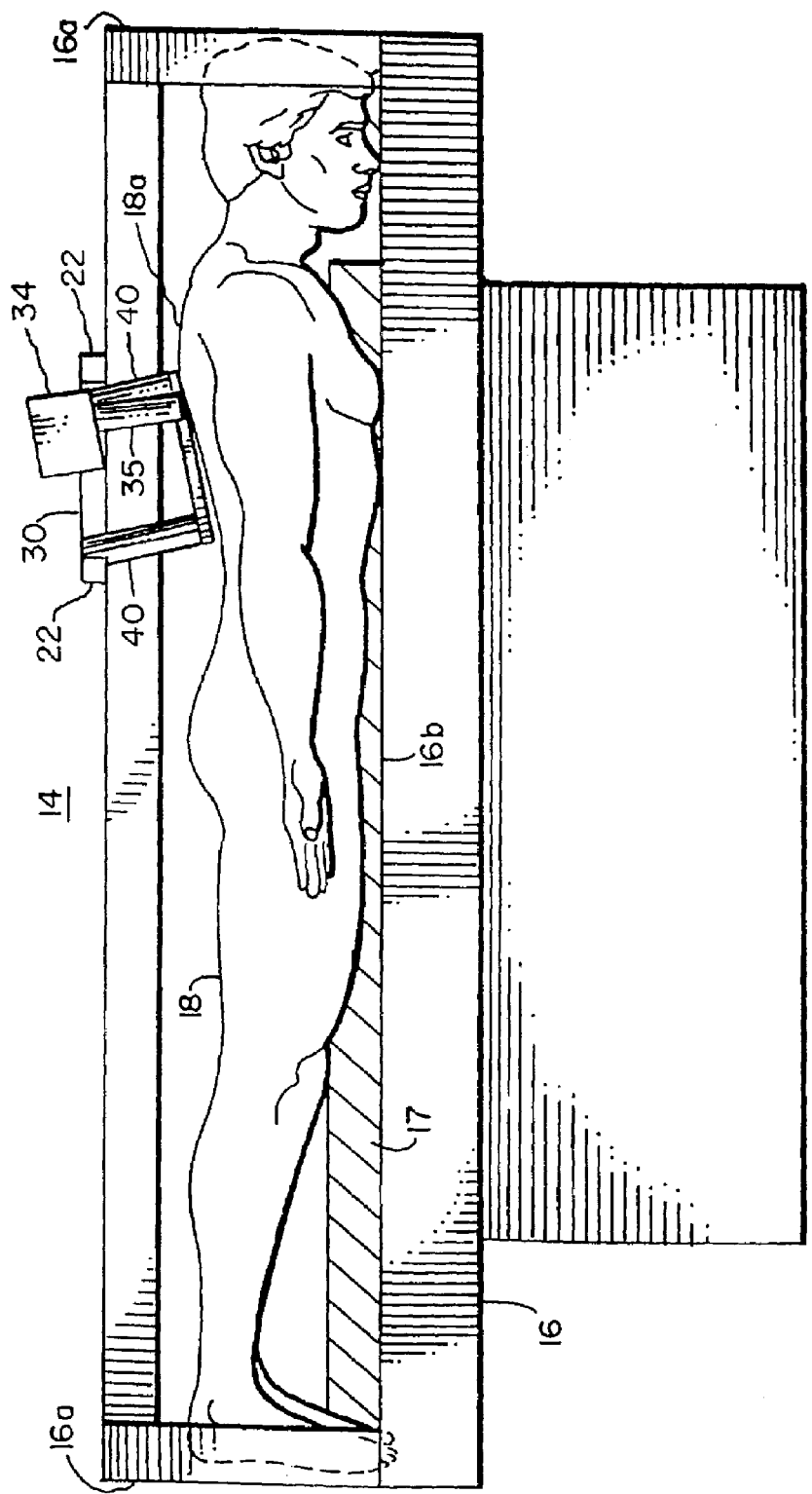
FIG. 1 is a side view of the system in accordance with a first embodiment of the present invention having the platen of the system in a down position.

Referring to FIGS. 1–4, there is shown system 14 including a rigid table 16 with a pad 17 on table surface 16a upon which a patient 18 may lay flat. Pad 17 may be composed of a vinyl-covered cell foam (such as CF 40100 Foam from EAR Specialty Composites of Indianapolis. Ind.) which deforms under the weight of patient 18 and remains deformed for a period of time after the patient has left the table. Table 16 has two parallel rails 20 spaced apart from each other along two opposite sides of table 16, and two parallel rails 22 spaced apart from each other. Rails 20 and 22 are perpendicular to each other, i.e., rails 20 extend in the x direction and rails 22 extend in the y direction.

A platen 30 carrying a confocal imaging head 34 is mounted in a mechanism provided by rails 20 and 22 for movably positioning head 34 to observe dermal tissue of interest in the body of patient 18. This mechanism has a carriage 25 supporting platen 30. Carriage 25 rides along rails 22 across table 16 (as indicated by bidirectional arrow x), and is locked in position with respect to rails 22 by a lock 28, such as a locking screw. Rails 22 and its two spacers 23, which connect rails 22 together, ride along rails 20 up or down table 16 (as indicated by bi directional arrow y), and are locked in position with respect to rails 20 by a lock 24, such as a locking screw. Thus, platen 30 can then be moved by the operator in two orthogonal directions x and y over patient 18 and temporarily fixed in a desired position.

Figure 4:
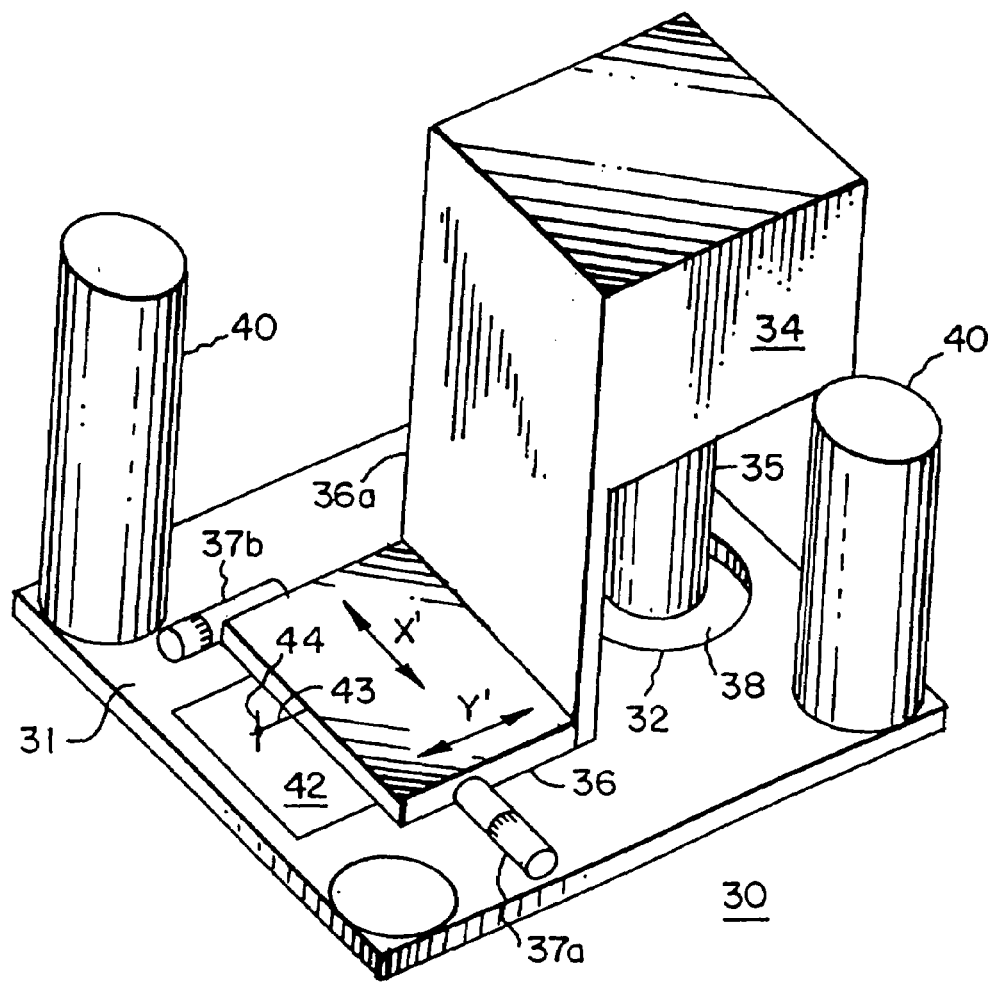
FIG. 4 is a perspective view of the platen of the system of FIG. 1.

Referring to FIG. 4, platen 30 and the head 34 assembly is shown in more detail. Platen 30 is a rigid structure having an upper surface 31 with a translation stage 36 which is mechanically coupled to a confocal imaging head 34 via support 36a. Confocal imaging head 34 has an objective lens 35 positioned over an orifice or opening 32 through platen 30. Confocal imaging head 34 with objective lens 35 are described in U.S. application Ser. No. 08/650,684, filed May 20, 1996, now U.S. Pat. No. 5,788,639, issued Aug. 4, 1998, and assigned to the same assignee as the present invention, and is herein incorporate y reference. Translation stage 36 is movable in two orthogonal directions x' and y' (see arrows x' and y' in FIG. 4) to provide fine resolution positioning (as compared with coarse positioning of platen 30 via rails 20 and 22) of imaging head 34, and more specifically objective lens 35, with respect to platen 30 over orifice 32. The translation stage 36 has cross rotating ball bearings (not shown) or cross piezoelectric position actuators to facilitate fine resolution movement in orthogonal directions x' and y'. Manual stage micrometers 37a and 37b adjust translation stage 36 in x' and y' directions, respectively. Micrometers 37a and 37b may be substituted by motors which are remotely controlled. A lock (not shown) on translation stage 36 may be provided to temporarily fix the position of stage 30, and consequently imaging head 22, with respect to platen 30. Thus, translation stage 36 defines a means for fine resolution positioning of the objective lens over the orifice. Also, an index matching plate 38 may be positioned within orifice 32 in front of objective lens 35 to form a window which maintains the height stability of the tissue while presenting the edges of orifice 32 to the skin for stressing the tissue.

Figure 2:
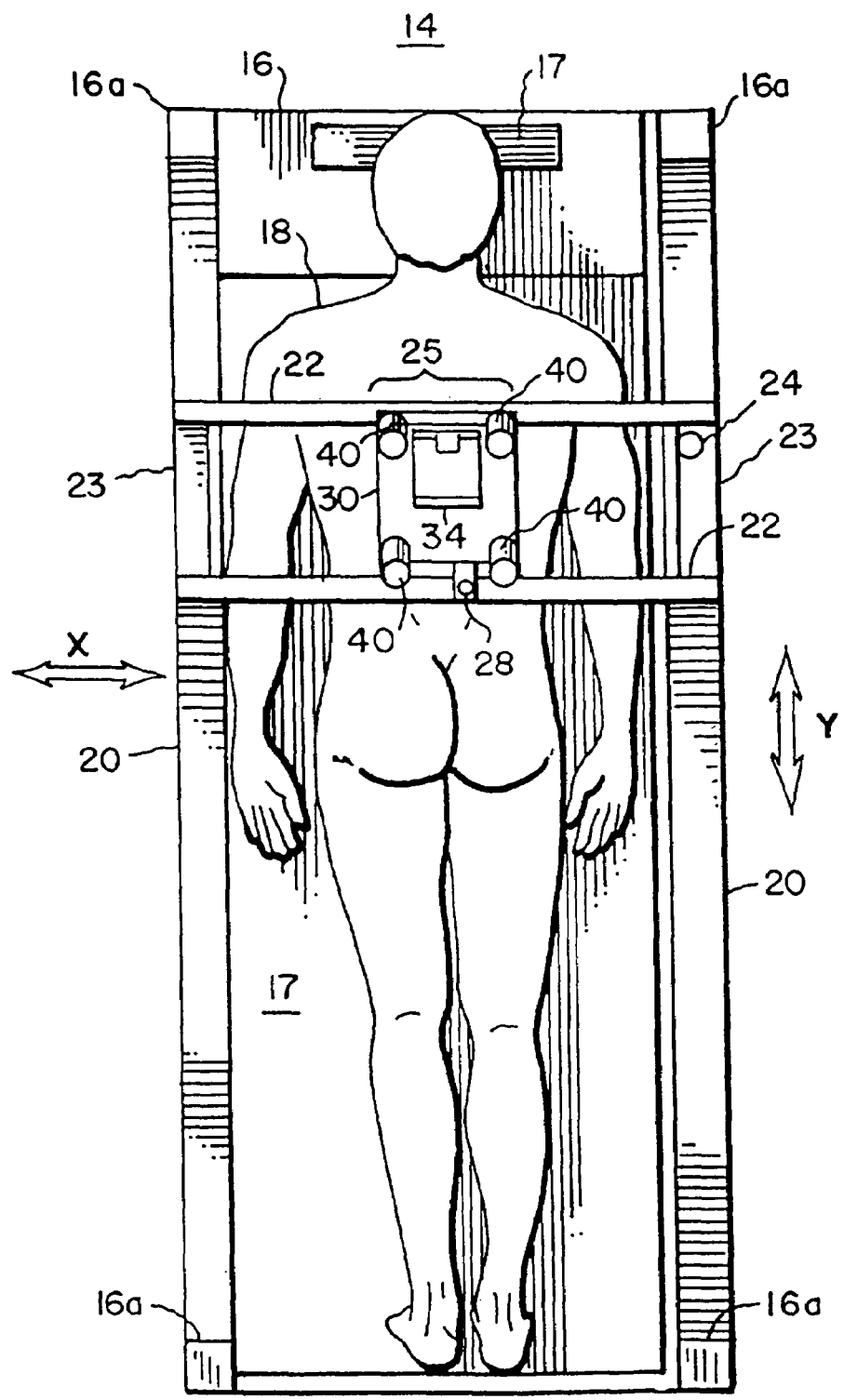
FIG. 2 is a plan view of the system of FIG. 1.
Figure 3:
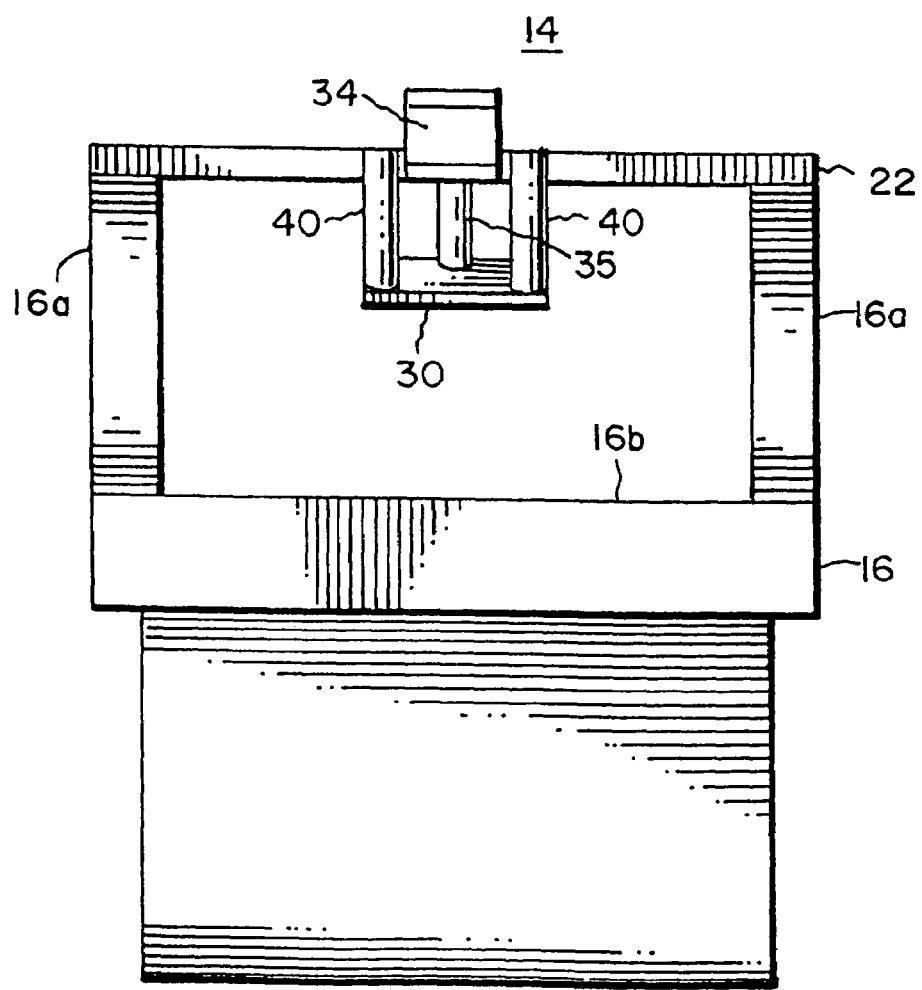
FIG. 3 is a front view of the system of FIG. 1 without the subject patient.

Platen 30 includes four vibration damping rods 40 at the four corners of platen 30 (for purposes of illustration only two rods 40 are shown in FIG. 4). Each damping rod 40 has a lower end coupled to platen 30 and an upper end coupled to carriage 25, as shown in FIGS. 1–3. Thus, damping rods 40 connect platen 30 to carriage 25. Damping rods 40 may be hydraulic type shock absorbers which when released allow platen 30 to gradually move from an up position to a down position upon the patient's skin 14a (such as shown in FIG. 1) and also allow platen 30 to be moved from a down position back to an up position. Locking screws (not shown) on the damping rods 40 may fix the position of platen 30 with respect to carriage 25 in either up or down positions. Damping rods 40 thereby provide a means for moving platen 30 from an up position, in which the platen is spaced from patient 18, to a down position onto surface 18a of skin tissue of the patient.

In operation of system 14, the operator (e.g., a physician) moves rails 22 (i.e., the rails upon which carriage 25 rides) along rails 20 to position platen 30 in the y direction, and moves carriage 25 along rails 22 to position platen 30 in the x-direction such that the volume of skin tissue of interest on patient 18, such as a lesion, will be positioned within orifice 23 of the platen when platen-30 is in a down position. Using locks 24 and 28 described above, the operator locks carriage 25 with respect to rails 20 and 22, thus fixing the position of platen 30 with respect to patient 18. Next, the operator releases damping rods 40 to allow platen 30 to gradually fall by the force of gravity onto the patient's skin. In response to the weight of platen 30, the skin lying within orifice 32 of platen 30 bulges upwards into orifice 32, thereby applying stress to the skin. This stress places the skin in orifice 32 preferably under tension, but may further push the skin up into orifice 32 by compression of skin beneath platen 30. The stress applied to the skin in orifice 32 is substantially due to the downward pressure or force of platen 30 at the edges of orifice 32. Optionally, springs may be located within damping rods 40 to provide additional downward pressure onto the skin. The operator then controls the translation stage movement either directly or remotely to position objective lens 35 of imaging head 34 over area of tissue within orifice 32 desired to be imaged. The operator enables optics within the confocal imaging head to confocally image horizontal, vertical, or angular sections through different planes of the tissue. During confocal imaging, the stress applied to the skin tissue in orifice 32 stabilize the tissue reducing motion of the skin tissue with respect to confocal imaging head 34, thereby stabilizing confocal images scanned by head 34.

Platen 30 may have a paper pad 42 to provide a recording media, and a pen or marker 44 mechanically coupled to translation stage 36 by arm 43 such that pen 44 is suspended over pad 42. Movement of translation stage 36 can thus be recorded by ink from the pen 44 on pad 32. This allows the operator during confocal imaging by imaging head 34 to map the horizontal extent or borders of a lesion in the skin, since pen 44 transfers the motion of translation stage 36 on pad 43 by the fixed geometry which mechanically couples pen 44 to objective lens 23 via arm 43, stage 36, support 36a and imaging head 34. After confocal imaging is complete, imaging head 34 may be replaced by another pen to permit the operator to trace the extent of the lesion recorded on pad 32 onto the surface of the skin.

Further, when platen 30 is in a down position, the operator can place index marks on the skin surface with a pen, or other marking instrument, at notches (not shown) along the sides of orifice 32. These index marks locate both orifice 32 and the relative position of objective lens 35 with respect to the skin surface when confocal imaging is performed. In subsequent examinations, orifice 32 and objective lens 35 can be aligned with these index marks to confocally image the same area of skin, and, for example, observe changes occurring in a skin lesion over time.

Figure 5:
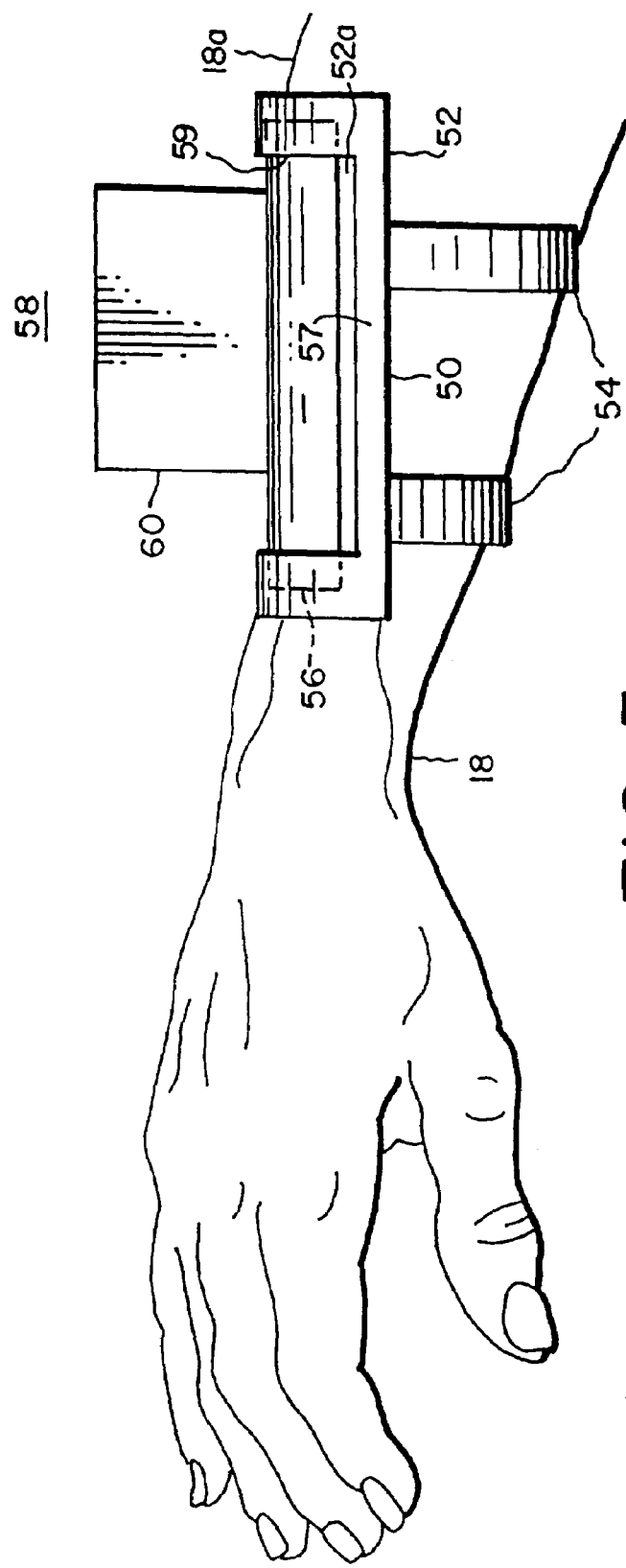
FIG. 5 is a side view of the system in accordance with a second embodiment of the present invention.
Figure 6:
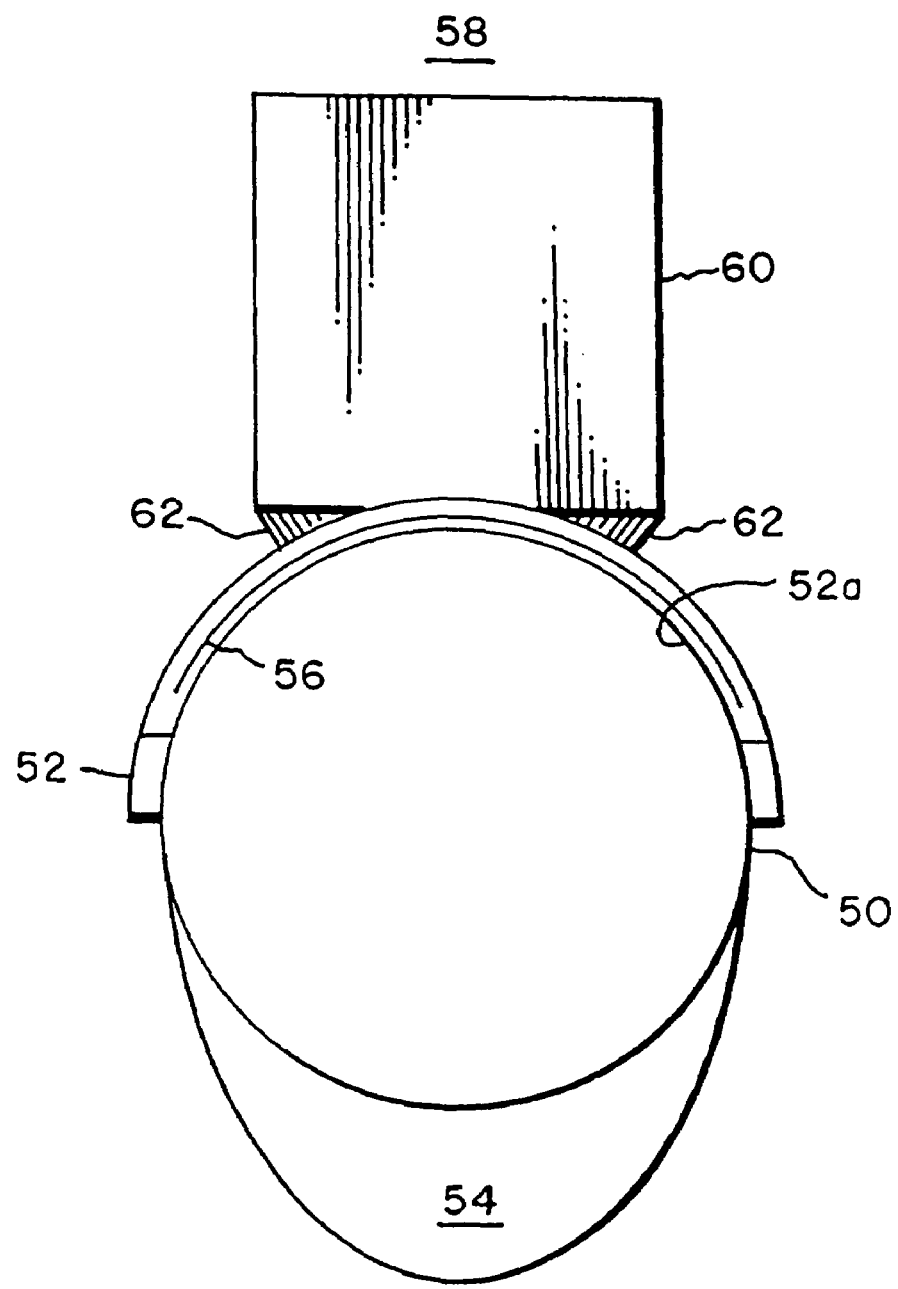
FIG. 6 is a front view of the system of FIG. 5 without the subject skin tissue.
Figure 7:
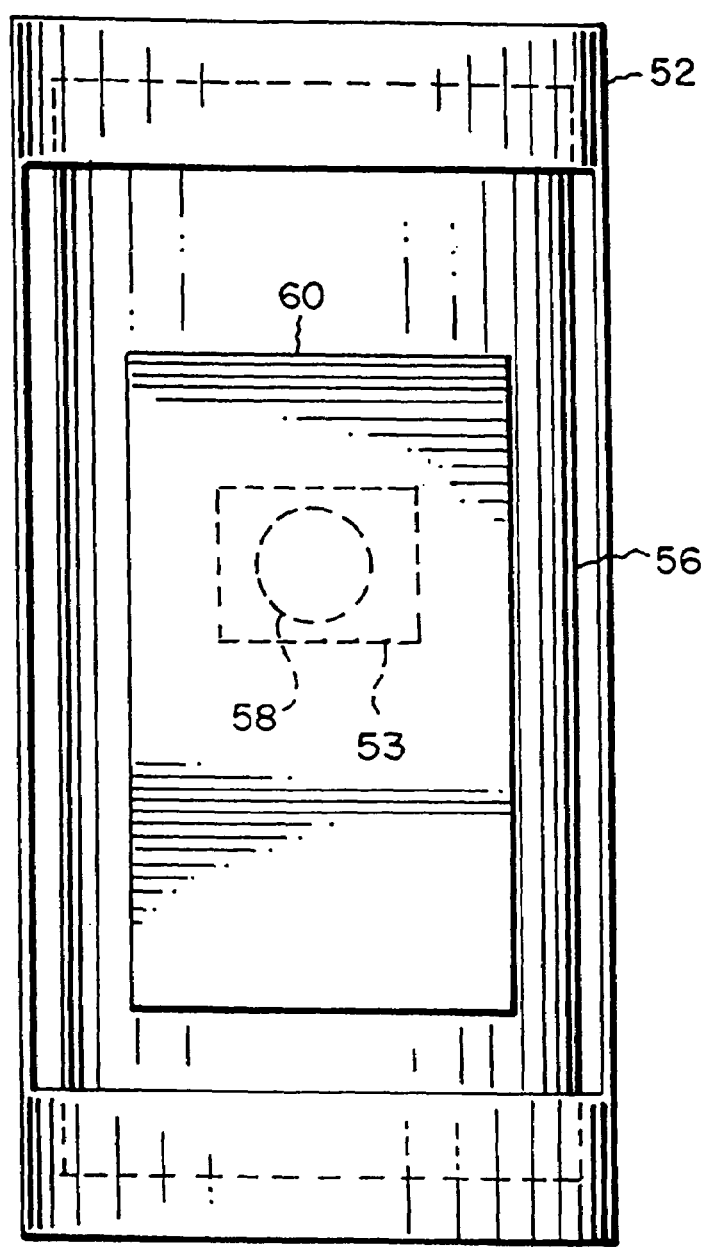
FIG. 7 is a plan view of the system of FIG. 5 without the subject skin tissue.
Figure 8:
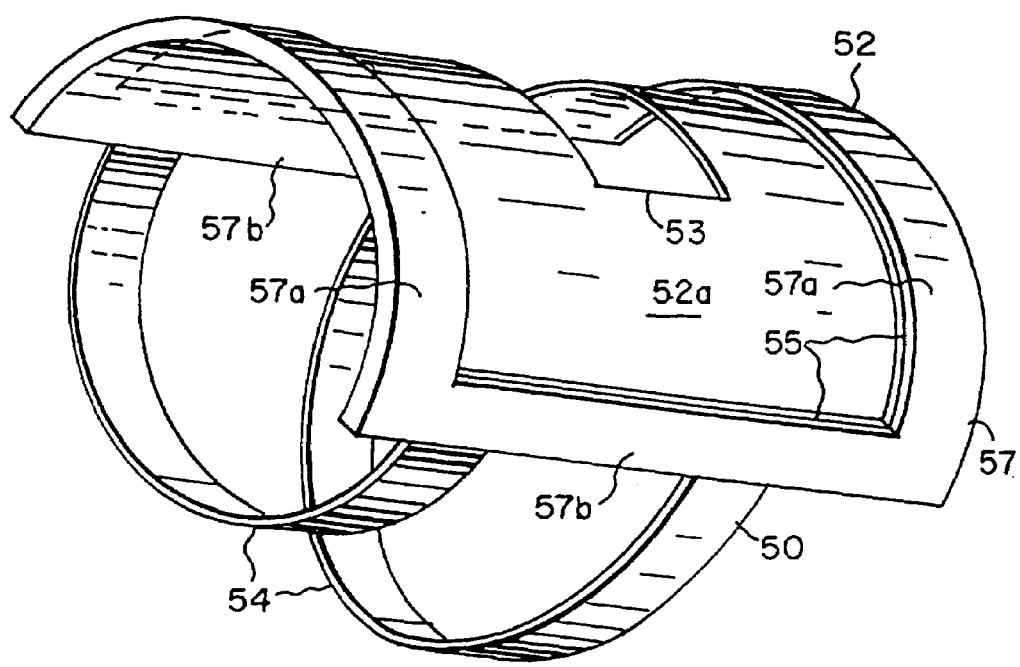
FIG. 8 is a perspective view of the brace structure of the system of FIG. 5 with the upper lamination of the brace structure and confocal imaging head removed.

A second embodiment of the present invention is shown in FIGS. 5–8 having a system 58. System 58 includes a brace structure 50 having a rigid lower lamination 52 which is held stationary to the skin tissue 18a of patient 18 by straps 54. Lower lamination 52 is shaped to approximate the curvature of a gross anatomical body part of the patient, such as part of the leg, torso, or arm, as shown in FIG. 5. A bottom 52a of lower lamination 52 has an opening 53, as shown in FIGS. 7 and 8. Bottom 52a defines a well 59 therein between ends 57a and sides 57b of lower lamination 52. Ends 57a and sides 57b define a rigid frame 57. Further, ends 57a and sides 57b have blind slots 55 within which an upper lamination 56 is captured. FIG. 8 shows frame 57 of lower lamination 52 in which upper lamination 56 has been removed for purposes of illustration.

Upper lamination 56 is a curved rigid sheet parallel with lower lamination 52, and has a confocal viewing window 58 (FIG. 7) substantially smaller than opening 53. Viewing window 58 may be positioned at a location over opening 53 by sliding upper lamination 56 over lower lamination 52 via slots 55 within frame 57. A confocal imaging head 60 is supported on brace structure 50 by gussets 62 (FIG. 6) and has an objective lens (not shown) positioned for imaging through confocal viewing window 58 of upper lamination 56. The window may contain a transparent plate for tissue height stabilization. Confocal imaging head 60 with the objective lens are described in U.S. application Ser. No. 08/650,684, filed May 20, 1996 now U.S. Pat. No. 5,788,639, issued Aug. 4, 1998, and assigned to the same assignee as the present invention, and is herein incorporated by reference. Confocal imaging head 60 is fixably attached to upper lamination 56 and slides therewith over lower lamination 52.

In operation of system 58, brace 50 is first strapped by straps 54 over an anatomical feature, such as an arm, leg, or torso, in which the general skin tissue area to be confocally imaged bulges upward through opening 53 of bottom 52a under the pressure from lower lamination 52, thereby applying stress to the surface of the skin. This stress preferably places the skin through opening 53 under tension, but may further push the skin up into opening 53 by compression of skin beneath lower lamination 52. The stress applied to the skin in opening 53 is substantially due to the pressure or force from lower lamination 52 to the skin tissue at the edges of opening 53. The specific area of the skin to be confocally imaged is then positioned within confocal viewing window 58 by sliding upper lamination 56 over lower lamination 52. Lower lamination 52 provides a sliding surface for upper lamination 56 and slots 55 of frame 57 provide sufficient friction against upper lamination 56 to temporarily fix the position of upper lamination 56 with respect to lower lamination 52 and the skin tissue. Confocal imaging head 60 is then attached to upper lamination 56 of brace 50 to position the confocal optics of head 60, i.e., its objective lens, through confocal imaging window 58. When enabled, these confocal optics within imaging head 60 can confocally image horizontal, vertical, or angular sections through different planes of the tissue through confocal viewing window 58. Thus, brace 50 locates confocal imaging head 60 in fixed relationship with the skin tissue, and window 58 defines an aperture through brace 50 for imaging via optics of head 60.

By attaching imaging head 60 to upper lamination 56, head 60 moves with motion of the skin tissue since such motion is transferred to head 60 via brace structure 50. This reduces the relative motion of the tissue held under stress with respect to the confocal optics of imaging head 60 to minimize instability of the confocal images from imaging head 60. Upper lamination 56 may be moved to reposition the confocal imaging optics of head 60 through window 58 for confocal imaging of other areas of skin tissue within opening 53.

Figure 9:
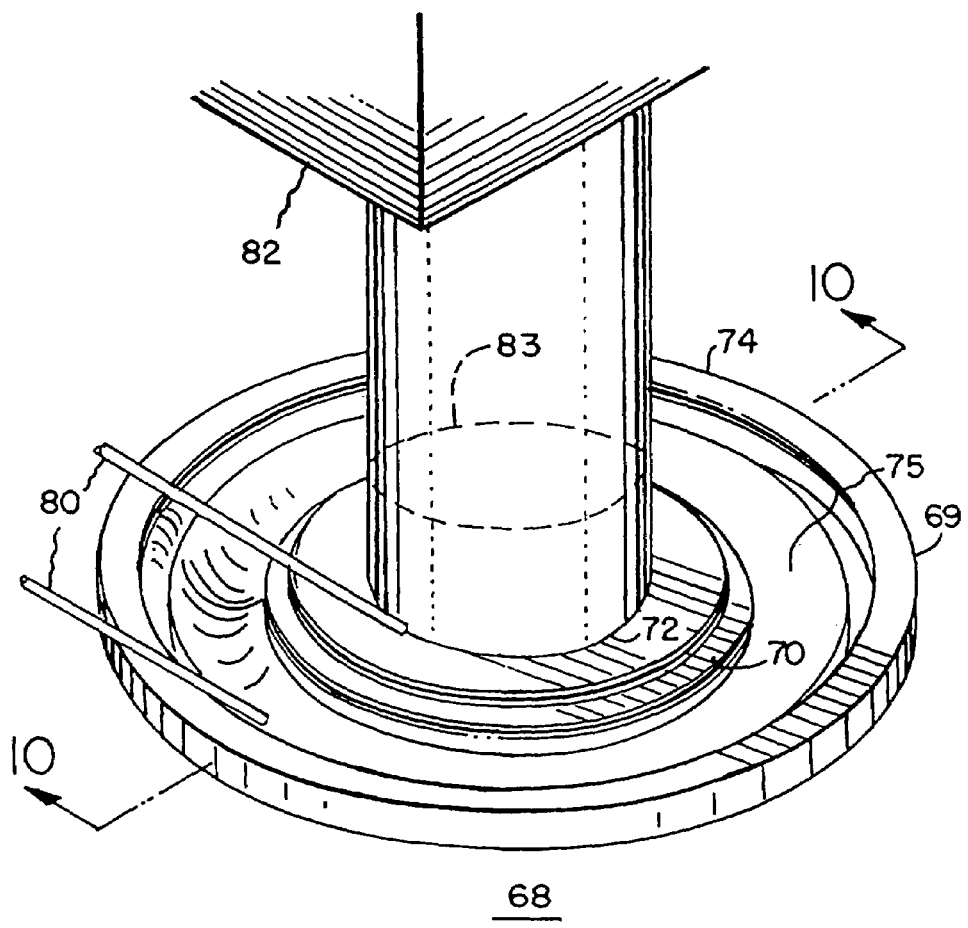
FIG. 9 is a perspective view of the system in accordance with a third embodiment of the present invention.
Figure 10:
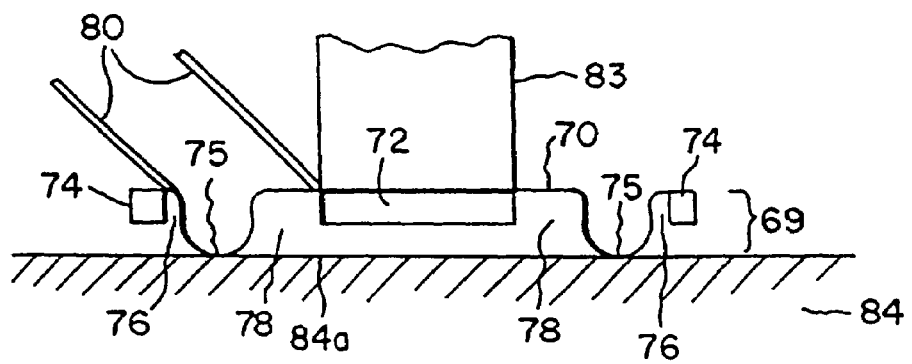
FIG. 10 is a cross-sectional view of the system along line 10—10 of FIG. 9 when the attachment of the system is not engaging skin tissue.
Figure 11:
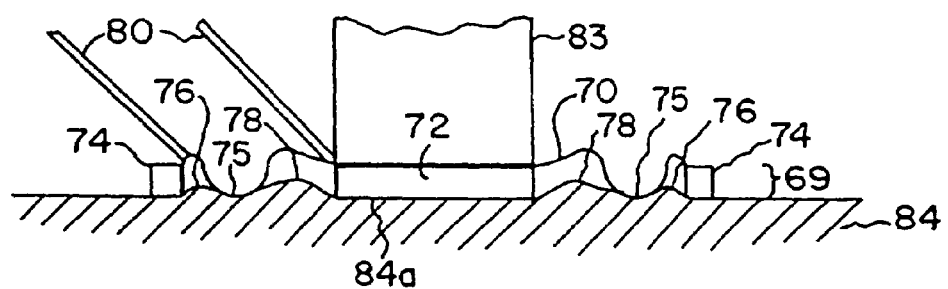
FIG. 11 is another cross-sectional view of the system along line 10—10 of FIG. 9 when the attachment of the system is engaging skin tissue.

A third embodiment of the present invention is shown in FIGS. 9–11. This embodiment is provided by a tissue stabilization system 68 which includes an attachment 69. The tissue is shown at 84 in FIGS. 10–11 as a layer of skin. Attachment 69 includes a flexible diaphragm member 70, a central circular window or plate member 72, and a semi-rigid ring 74. Diaphragm 70 is composed of deformable rubber selected to be less compliant than tissue 84. Diaphragm 70 radially extends from window 72 outward to semi-rigid ring 74. Ring 74 may be composed of hard rubber, while window 72 may be composed of a material having an optical index approximately matching tissue 84. Diaphragm 70 has between ring 74 and window 72 an annular protruding section 75 (protruding in the direction of the arrow of FIG. 10). Section 75 defines outer and inner annular cavities 76 and 78, respectively. Also, attachment 69 has a pair of vacuum lines 80 which each connects different ones of annular cavities 76 and 78 to a pneumatic pump which selectively creates suction between diaphragm 70 and the surface 84a of tissue 84. The size or diameter of system 68 and its attachment 69 may be appropriately dimensioned for the skin surface area to be confocally imaged through window 72.

System 68 further includes a confocal imaging head 82 having an objective lens 83 positioned such that lens 83 is directed to window 72 of attachment 69. Confocal imaging head 82 with objective lens 83 are described in U.S. application Ser. No. 08/650,684, filed May 20, 1996, now U.S. Pat. No. 5,788,639, issued Aug. 4, 1998, and assigned to the same assignee as the present invention, and is herein incorporated by reference. Objective lens 83 is shown in phantom lines in FIG. 9, and the dotted lines in the figure represent the optical imaging paths between lens 83 and other confocal optics within imaging head 82. For example, these optical imaging paths may be provided within an extending snout between head 82 and objective lens 83.

In operation, attachment 69 is first placed over surface 84a of tissue 84 such that diaphragm protruding section 75 is adjacent to surface 84a, as shown in FIG. 10. When window 72 is located over the area of tissue 84 to be confocally imaged, the air is evacuated via vacuum lines 80 from each cavity 76 and 78. This creates suction which pulls tissue 84 up into cavities 76 and 78, as shown in FIG. 11. As a result, semi-rigid ring 74 and window 72 are pulled downward onto surface 84, and the tissue beneath window 72 is placed under stress, such as by tension or compression. In this mode, attachment 69 engages or adheres by suction to the surface 84a of the tissue.

Next, objective lens 83 of confocal imaging head 82 is placed against window 72 for confocal imaging of tissue 84 below window 72, then the confocal optics within imaging head 60 are enabled to provide confocal images of horizontal, vertical and angular sections through different planes of the tissue. Optionally, attachment 69 may be fixedly attached to head 82 in front of its objective lens 83 prior to placing attachment 69 adjacent to the skin tissue. Since the tissue being confocally imaged is held under stress by attachment 69 under window 72, the relative motion of this tissue with respect to the confocal optics within imaging head 82 is reduced, thereby stabilizing confocal images from head 82. When imaging is complete, air is allowed to flow back into cavities 76 and 78 via vacuum lines 80, allowing attachment 69 to disengage from the surface 84a of the tissue.

Alternatively, a liquid on the surface 84a of the tissue may be evacuated via vacuum lines 80 (in combination with or instead of air) from cavities 76 and 78. Such a liquid may be applied to the surface 84a of the tissue prior to placing attachment 69 over the surface.

Each of the three embodiments of the present invention is particularly suitable for imaging external tissue in different regions of the patient's body. The first embodiment may be used for confocal imaging of skin tissue on the chest or back, while the second embodiment may be used for gross anatomical features, such as the arm or leg, around which straps can hold brace structure 50 upon. Further, the third embodiment is useful for smaller regions of the skin, particularly where there is no gross anatomical feature, or where the surface of the skin tissue in not substantially level, such as the cervix or forehead. Each of the above confocal imaging system embodiments provides a mechanism for maintaining an area of skin tissue being confocal imaged under a stressed configuration by tension or compression, thereby minimizing the motion of this area with respect to a confocal imaging head. In the cervix the tissue being imaged is not skin as that term is commonly understood, but represents internal tissue of a patient. Internal tissues, for example which are surgically exposed, may be stabilized using the invention.

From the foregoing description, it will be apparent that there have been provided several embodiments of a confocal imaging system for dermatological pathology applications. Variations and modifications of the herein described system and other applications for the invention will undoubtedly suggest themselves to those skilled in the art. Accordingly, the foregoing description should be taken as illustrative and not in a limiting sense.

What is claimed is:

1. A system for dermatological examination of the skin tissue of a patient comprising:
   a plate;
   means for maintaining an area of the skin tissue under stress by application of force against said plate, in which said maintaining means comprises a member extending from said plate; and
   an imaging head, coupled to said maintaining means, capable of producing one or more images representing optically formed sections of said stressed skin tissue from light returned through said plate from focused light under the surface of said skin tissue to provide therewith an integrated assembly in which said stress applied to said tissue stabilizes said skin tissue with respect to said imaging head, wherein said imaging head comprises at least an objective lens for focusing the light under the surface of said skin tissue and collecting the returned light through said plate, and at least one actuator capable of moving said objective lens to change location of said focusing in said tissue.

2. The system according to claim 1 wherein said member comprises a platen which is positionable with respect to said patient, said platen having an orifice, and said imaging head being coupled to said platen and positioned for imaging through said surface and said plate; and
   first means for moving said platen from an up position in which said platen is spaced from said patient to a down position onto the surface of said skin tissue of the patient, whereby in said down position the force of said platen provides said stressed skin tissue within said orifice.

3. The system according to claim 2 wherein said maintaining means further comprises:
   second means coupled to said platen for moving said platen with respect to said patient and temporarily fixing the position of said platen so that said skin tissue to be imaged is located within said orifice when said first means moves said platen to said down position.

4. The system according to claim 2 wherein said maintaining means further comprises:
   means coupled to said imaging head and said platen for translating said imaging head with respect to said orifice of said platen.

5. The system according to claim 2 wherein said orifice has said plate positioned therein.

6. The system according to claim 1 wherein said imaging head is a confocal imaging head having confocal imaging optics for providing images of section of said stressed skin tissue.

7. The system according to claim 1 wherein said member comprises a platen having means through which said tissue is imaged by said imaging head.

8. The system according to claim 7 wherein said platen is positionable with respect to said tissue.

9. The system according to claim 1 further comprising means for fixing the position of said member with respect to said patient.

10. The system according to claim 1 wherein said imaging head is movable with respect to said maintaining means to position said imaging head with respect to said stressed tissue.

11. The system according to claim 1 wherein said maintaining means applies force against at least the edges of said area of the skin tissue.

12. The system according to claim 1 wherein said section represents one of a horizontal, vertical or angled section through said tissue.

13. A system for dermatological examination of the skin tissue of a patient comprising:
   means for maintaining an area of the skin tissue under stress by application of force, and an imaging head, coupled to said maintaining means, capable of imaging a section of said stressed skin tissue to provide therewith an integrated assembly, wherein said maintaining means further comprises:
a platen which is positionable with respect to said patient, said platen having an orifice, and said imaging head being coupled to said platen and positioned for imaging through said orifice;
first means for moving said platen from an up position in which said platen is spaced from said patient to a down position onto the surface of said skin tissue of the patient, whereby in said down position the force of said platen provides said stressed skin tissue within said orifice; and
second means coupled to said platen for moving said platen with respect to said patient and temporarily fixing the position of said platen so that said skin tissue to be imaged is located within said orifice when said first means moves said platen to said down position, wherein said second means further comprises:
a table having a surface supporting said patient and two opposing sides spaced apart from each other on opposite sides of said patient;
two first rails, each of said first rails being parallel to each other and located upon a different one of said opposing sides;
two second rails orthogonal to said first rails which are parallel to each other and movable together along said first rails;
a carriage supporting said platen which is movable along said second rails;
means for locking said second rails at a position with respect to said first rails; and
means for locking said carriage at a position with respect to said second rails.

14. The system according to claim 13 wherein said first means comprises a plurality of rods coupling said platen to said carriage for positioning said platen in one of said up and down positions.

15. A system for dermatological examination of the skin tissue of a patient comprising:
means for maintaining an area of the skin tissue under stress by application of force, and
an imaging head, coupled to said maintaining means, capable of imaging a section of said stressed skin tissue to provide therewith an integrated assembly, wherein said maintaining means further comprises:
a platen which is positionable with respect to said patient, said platen having an orifice, and said imaging bead being coupled to said platen and positioned for imaging through said orifice;
first means for moving said platen from an up position in which said platen is spaced from said patient to a down position onto the surface of said skin tissue of the patient, whereby in said down position the force of said platen provides said stressed skin tissue within said orifice; and
means coupled to said imaging head and said platen for translating said imaging head with respect to said orifice of said platen, wherein said platen further comprises a recording media, and said translating mean further comprises a translation stage and a marker coupled to said translation stage which is positioned over said media to record the motion of said translating stage as it moves said imaging head over said stressed tissue within said orifice.

16. An apparatus for stabilizing the skin tissue of a patient to an imaging head comprising:
a platen having an orifice;
first means for moving said platen from an up position in which said platen is spaced from said patient to a down position onto the surface of said skin tissue of the patient; and
second means for moving said platen over the patient and temporarily fixing the position of the platen with respect to said patient wherein the skin tissue to be imaged via said orifice by said imaging head is stabilized when said platen is in a down position, wherein said second means further comprises:
a table having a surface supporting said patient and two opposing sides spaced apart from each other on opposite sides of said patient;
two first rails, each of said first rails being parallel to each other and located upon a different one of said opposing sides;
two second rails orthogonal to said first rails which are parallel to each other and movable together along said first rails;
a carriage supporting said platen which is movable along said second rails;
means for locking said second rails at a position with respect to said first rails; and
means for locking said carriage at a position with respect to said second rails.

17. The system according to claim 16 wherein said first means comprises a plurality of rods coupling said platen to said carriage for positioning said platen in one of said up and down positions.

18. The system according to claim 16 wherein said maintaining means further comprises:
means, coupled to said imaging head and said platen, for translating said imaging head with respect to said orifice of said platen.

19. A system for examining tissue comprising:
a plate;
means for maintaining an area of the tissue under stress by application of force of said plate upon said tissue, in which said maintaining means comprises a member extending from said plate; and
an imaging head, coupled to said maintaining means, capable of imaging said stressed tissue through said plate from light returned from a scanned focal spot through said tissue to provide an image of a section, wherein said imaging head comprises at least an objective lens for focusing the light under the surface of said skin tissue and collecting the returned light through said plate, and at least one actuator capable of moving said objective lens to change location of said focusing in said tissue.

20. The system according to claim 19 wherein said tissue represents one of skin tissue and internal tissue.

21. The system according to claim 19 wherein said maintaining means applies force against at least the edges of said area of the tissue.

22. The system according to claim 19 wherein said imaging head is movable with respect to said maintaining means to position said imaging head with respect to said stressed tissue.

23. A method for examination of tissue comprising the steps of:
providing a platen having an opening with a plate;
maintaining an area of the tissue under stress by application of said platen upon said tissue; and optically forming one or more images of a section of said stressed tissue via an objective lens through said opening of said platen from light returned from focused light under the surface of said skin tissue in which said stress applied to said tissue promotes stabilization of said tissue with respect to images produced by said imaging step; and positioning said objective lens within a housing having said objective lens to adjust at least the depth of said images of said sections in said skin tissue.

24. The method according to claim 23 further comprising the step of:

positioning said platen with respect to the area of the tissue to be imaged.

25. An apparatus for dermatological examination of the tissue of a patient comprising:

a plate;

means for maintaining an area of the skin tissue under stress by application of force against said plate, in which said maintaining means comprises a member extending from said plate; and means for imaging said tissue through said plate, said imaging means being coupled to said maintaining means and capable of producing images representing optically formed sections through different planes of said stressed tissue in which said stress applied to said tissue stabilizes said tissue with respect to said imaging head, in which said imaging means comprises optics and said maintaining means limits view of said tissue by said optics, wherein said optics are movable to focus and collect light from different locations of said tissue in said limited view provided by said maintaining means.

26. The system according to claim 25 wherein said sections are one of horizontal, vertical, or angled sections through said different planes of said stressed tissue.

27. The system according to claim 25 wherein said imaging means images said sections of said stressed skin tissue from light returned from focused light under the surface of said tissue.

28. The system according to claim 25 wherein said member comprises one of a platen, brace, or deformable diaphragm.

29. A system for examination of tissue of a patient comprising:

a member having a surface, said member being positionable for compressing and maintaining an area of the tissue under stress by application of force against said surface, in which said member has an opening;

a material window; and an imaging head, coupled to said member, capable of producing one or more images representing optically formed sections at desired orientations and depths within said stressed tissue from light returned through said opening and said material window from focused light under the surface of said tissue, in which said stress applied to said tissue stabilizes said tissue, wherein said imaging head comprises optics for focusing the light under the surface of said skin tissue through said opening and said window, and collecting the returned light through opening and said window, and said optics are movable to select at least the depth of said images of said sections in said skin tissue.

30. The system according to claim 29 wherein said surface of said member is one of flat, curved, or deformable.

31. A system for examination of tissue of a patient comprising:

a member positionable against tissue for compressing and maintaining an area of the tissue under stress by application of a non-suctioning force, in which said member has an opening;

a material window; and an imaging head, coupled to said member, capable of producing one or more images of optically formed sections within said stressed tissue via said opening and said material window, in which said stress applied to said tissue stabilizes said tissue.

32. The system according to claim 31 wherein said member is one of a platen or brace.

33. An apparatus for stabilizing the skin tissue of a patient to an imaging head comprising a carriage having a platen with an orifice positionable over the skin tissue of a patient, said carriage being positionable along a first path with respect to said skin tissue, and positionable along a second path with respect to said skin tissue, in which said first and second paths are orthogonal to each other, and when said carriage is positioned along said first and second paths said platen is positionable onto the patient to locate the orifice with respect to the skin tissue to be imaged.

34. The apparatus according to claim 33 wherein said apparatus further comprises a material window in which the skin tissue is imagable by said imaging head through said material window and said orifice.

35. The apparatus according to claim 33 wherein said platen supports the imaging head, and the imaging head is positionable with respect to said orifice of said platen.

* * * * *

UNITED STATES PATENT AND TRADEMARK OFFICE
CERTIFICATE OF CORRECTION

PATENT NO.        : 7,225,010 B1
APPLICATION NO.   : 09/658736
DATED             : May 29, 2007
INVENTOR(S)       : Zavislan It is certified that error appears in the above-identified patent and that said Letters Patent is hereby corrected as shown below:

On the title page, under the heading "OTHER PUBLICATIONS", please add the following:

-- Maurice, D., A Scanning Slit Optical Microscope, Investigative Ophthalmology, Vol. 13, No. 12, pp. 1033-1037, 1974.--

Signed and Sealed this

Twenty-third Day of October, 2007

JON W. DUDAS
*Director of the United States Patent and Trademark Office*